US010191270B2

(12) United States Patent
Igarashi (10) Patent No.: US 10,191,270 B2
(45) Date of Patent: Jan. 29, 2019

(54) IMAGING UNIT AND ENDOSCOPE APPARATUS (71) Applicant: OLYMPUS CORPORATION, Tokyo (JP)

(72) Inventor: Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 205 days.

(21) Appl. No.: 14/931,070

(22) Filed: Nov. 3, 2015

(65) Prior Publication Data
US 2016/0054559 A1 Feb. 25, 2016

Related U.S. Application Data (63) Continuation of application No. PCT/JP2014/062572, filed on May 12, 2014.

(30) Foreign Application Priority Data

Jun. 28, 2013 (JP) .................. 2013-136561

(51) Int. Cl.
G02B 23/24 (2006.01)
H04N 13/00 (2018.01)
(Continued)

(52) U.S. Cl.
CPC .......... *G02B 23/2484* (2013.01); *A61B 1/051* (2013.01); *G02B 23/2476* (2013.01);
(Continued)

(58) Field of Classification Search
None
See application file for complete search history.

(56) References Cited

U.S. PATENT DOCUMENTS 6,567,115 B1 * 5/2003 Miyashita et al. ..... A61B 1/051 348/76
2004/0218084 A1 11/2004 Komoro et al.
2014/0003018 A1 1/2014 Fujimori

FOREIGN PATENT DOCUMENTS

JP 06005828 A * 1/1994 ....... H01L 27/14618
JP H06-005828 A 1/1994
(Continued)

OTHER PUBLICATIONS

Extended Supplementary European Search Report dated Jan. 30, 2017 in European Patent Application No. 14 81 8818.8.
(Continued)

Primary Examiner — Anand S Rao
Assistant Examiner — Tyler B Edwards
(74) Attorney, Agent, or Firm — Scully, Scott, Murphy & Presser, P.C.

(57) ABSTRACT

An imaging unit includes: a solid state image sensor configured to receive light and perform photoelectric conversion on the light to generate an electric signal; a substrate extending from the solid state image sensor in an optical axis direction of the solid state image sensor; and a multi-layer substrate formed on a surface of the substrate, the multi-layer substrate having a plurality of electronic components mounted thereon and having a plurality of conductor layers and a plurality of via holes formed therein. At least one of the plurality of electronic components is embedded inside the multi-layer substrate. The plurality of via holes is formed on an outer side of the at least one of the plurality of electronic components embedded inside the multi-layer substrate along an optical axis direction of the multi-layer substrate.

8 Claims, 8 Drawing Sheets (51) Int. Cl.
  *H04N 5/225* (2006.01)
  *A61B 1/05* (2006.01)
  *H05K 1/02* (2006.01)
  *H05K 1/11* (2006.01)
(52) U.S. Cl.
  CPC ......... *H04N 5/2253* (2013.01); *H05K 1/0271* (2013.01); *H05K 1/115* (2013.01); *H04N 2005/2255* (2013.01)

(56) References Cited

FOREIGN PATENT DOCUMENTS

| | | |
|---|---|---|
| JP | H06-085465 A | 3/1994 |
| JP | H11-330639 A | 11/1999 |
| JP | 2000-199863 A | 7/2000 |
| JP | 2005-304876 A | 11/2005 |
| JP | 2009-049973 A | 3/2009 |
| JP | 2009-247621 A | 10/2009 |
| JP | 2010-103628 A | 5/2010 |
| JP | 2011-050496 A | 3/2011 |
| JP | 2011-050497 A | 3/2011 |
| JP | 2011050497 A * | 3/2011 |
| JP | 2011050497 A * | 3/2011 |
| JP | 2012-186301 A | 9/2012 |
| WO | 2012/120742 A1 | 9/2012 |

OTHER PUBLICATIONS

Japanese Office Action dated May 23, 2017 in Japanese Patent Application No. 2013-136561.
International Search Report dated Jun. 24, 2014 issued in PCT/JP2014/062572.

* cited by examiner

IMAGING UNIT AND ENDOSCOPE APPARATUS

CROSS-REFERENCE TO RELATED APPLICATIONS

This application is a continuation of PCT international application Ser. No. PCT/JP2014/062572 filed on May 12, 2014 which designates the United States, incorporated herein by reference, and which claims the benefit of priority from Japanese Patent Application No. 2013-136561, filed on Jun. 28, 2013, incorporated herein by reference.

BACKGROUND

1. Technical Field

The disclosure relates to an imaging unit provided at a distal end of an insertion unit of an endoscope that is configured to be inserted into a subject for capturing an image of an inside the subject, and relates to an endoscope apparatus.

2. Related Art

In medical and industrial fields, endoscope apparatuses have conventionally been used widely in a variety of examinations. Among these endoscope apparatuses, a medical endoscope apparatus has been used widely since it is capable of obtaining an in-vivo image inside a body cavity without incising the subject by inserting a flexible insertion unit, which has an elongated shape and is provided with an imaging element at a distal end thereof, inside the body cavity of the subject such as a patient, and furthermore, it is capable of performing a therapeutic treatment as necessary by protruding a treatment tool from the distal end of the insertion unit.

An imaging unit including an imaging element and a lens unit that performs image-formation of a subject image on a light-receiving surface of the imaging element (for example, see JP 2005-304876 A) are fitted to the distal end of the insertion unit of such endoscope apparatus.

Figure 11:
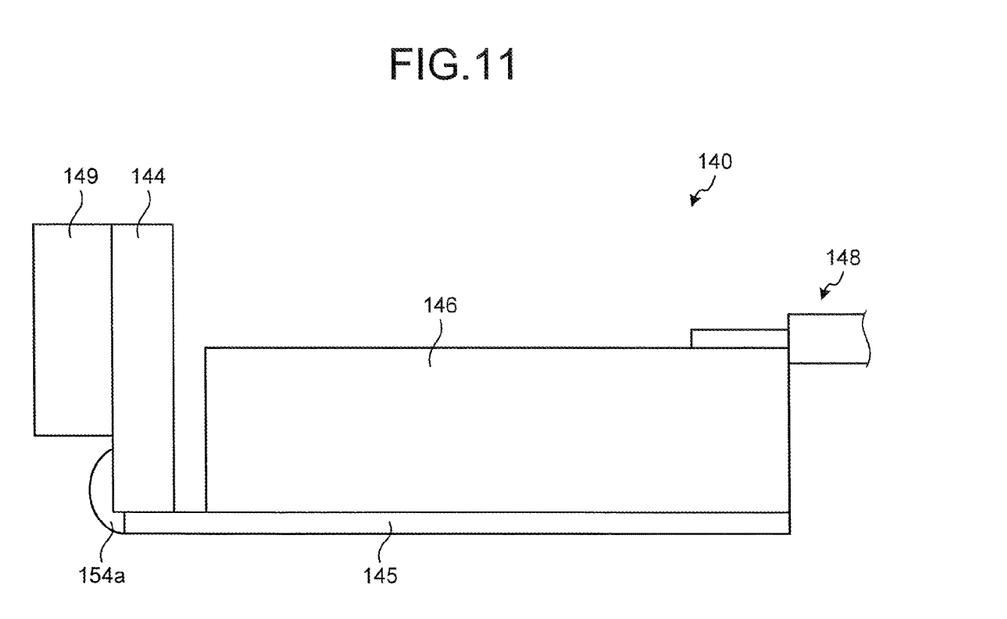
FIG. 11 is a schematic view illustrating a conventional imaging unit.

FIG. 11 is a schematic view illustrating a conventional imaging unit. In FIG. 11, the imaging unit is viewed in a direction orthogonal to an optical axis direction and orthogonal to a stacking direction of a multi-layer substrate. As illustrated in FIG. 11, a conventional imaging unit 140 has a configuration in which a substrate 145 extends in the optical axis direction from an imaging element 144. The imaging element 144 has a light-receiving surface covered with a glass lid 149. The substrate 145 is electrically connected to the imaging element 144 by an inner lead, which is not illustrated, and a connected part thereof is sealed with an adhesive 154a. A multi-layer substrate 146 is formed on the substrate 145, and a distal end of a signal cable 148 is connected to a proximal end portion of the multi-layer substrate 146.

Figure 12A:
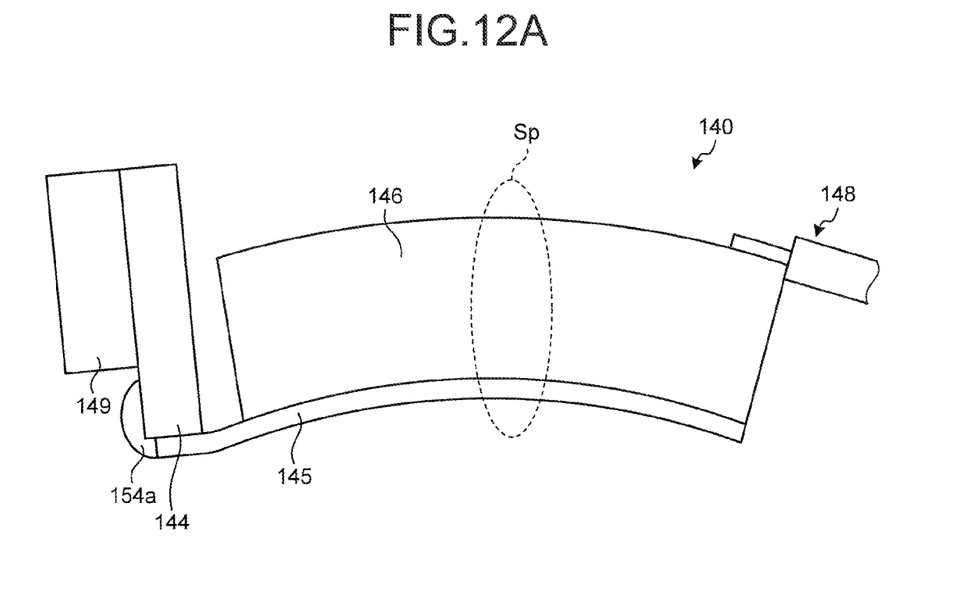
FIG. 12A is a schematic view illustrating a force applied to the imaging unit.
Figure 12B:
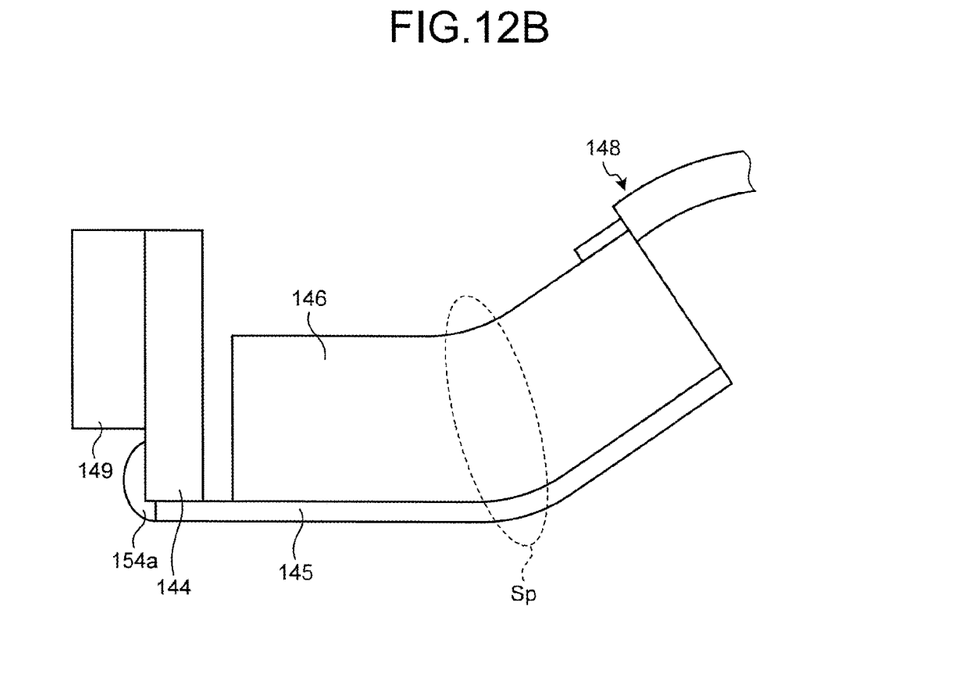
FIG. 12B is a schematic view illustrating the force applied to the imaging unit.

In an endoscope apparatus, accompanied with forward and backward operation of an insertion unit as well as a bending movement thereof for adjusting a camera angle during use of an endoscope, a force pushing in a distal end direction or a force shaking up and down and twisting is applied to the signal cable 148. This causes an upward or downward stress on the substrate 145 and the multi-layer substrate 146 to which the signal cable 148 is connected. Accordingly, as illustrated in FIGS. 12A and 12B, a central part Sp of the substrate 145 and the multi-layer substrate 146 may be bent. In an imaging unit of the endoscope, a central part of the substrate may be warped by heat and a load during manufacturing of the imaging unit. In the endoscope apparatus, a compact imaging unit has been promoted to reduce a diameter of the insertion unit; however, as the imaging unit becomes smaller, an influence of this bending stress becomes non-negligible, whereby performance of the imaging unit may be degraded.

SUMMARY

In some embodiments, an imaging unit includes: a solid state image sensor configured to receive light and perform photoelectric conversion on the light to generate an electric signal; a substrate extending from the solid state image sensor in an optical axis direction of the solid state image sensor; and a multi-layer substrate formed on a surface of the substrate, the multi-layer substrate having a plurality of electronic components mounted thereon and having a plurality of conductor layers and a plurality of via holes formed therein. At least one of the plurality of electronic components is embedded inside the multi-layer substrate. The plurality of via holes is formed on an outer side of the at least one of the plurality of electronic components embedded inside the multi-layer substrate along an optical axis direction of the multi-layer substrate.

In some embodiments, an endoscope apparatus includes an insertion unit having an imaging unit at a distal end of the insertion unit. The imaging unit includes: a solid state image sensor configured to receive light and perform photoelectric conversion on the light to generate an electric signal; a substrate extending from the solid state image sensor in an optical axis direction of the solid state image sensor; and a multi-layer substrate formed on a surface of the substrate, the multi-layer substrate having a plurality of electronic components mounted thereon and having a plurality of conductor layers and a plurality of via holes formed therein. At least one of the plurality of electronic components is embedded inside the multi-layer substrate. The plurality of via holes is formed on an outer side of the at least one of the plurality of electronic components embedded inside the multi-layer substrate along an optical axis direction of the multi-layer substrate.

The above and other features, advantages and technical and industrial significance of this invention will be better understood by reading the following detailed description of presently preferred embodiments of the invention, when considered in connection with the accompanying drawings.

DETAILED DESCRIPTION

Reference will be made below to an endoscope apparatus provided with an imaging unit as modes for carrying out the present invention (hereinafter, referred to as "embodiment(s)"). The present invention is not to be limited by the embodiment(s). The same reference signs are used to refer to the same elements throughout the drawings. The drawings are schematic, and it is to be noted that a relationship between thickness and width of each member, a ratio between each of the members, and the like may be different from actualities. Also, there may be a part having a difference in size or ratio between the drawings.

Embodiment

Figure 1:
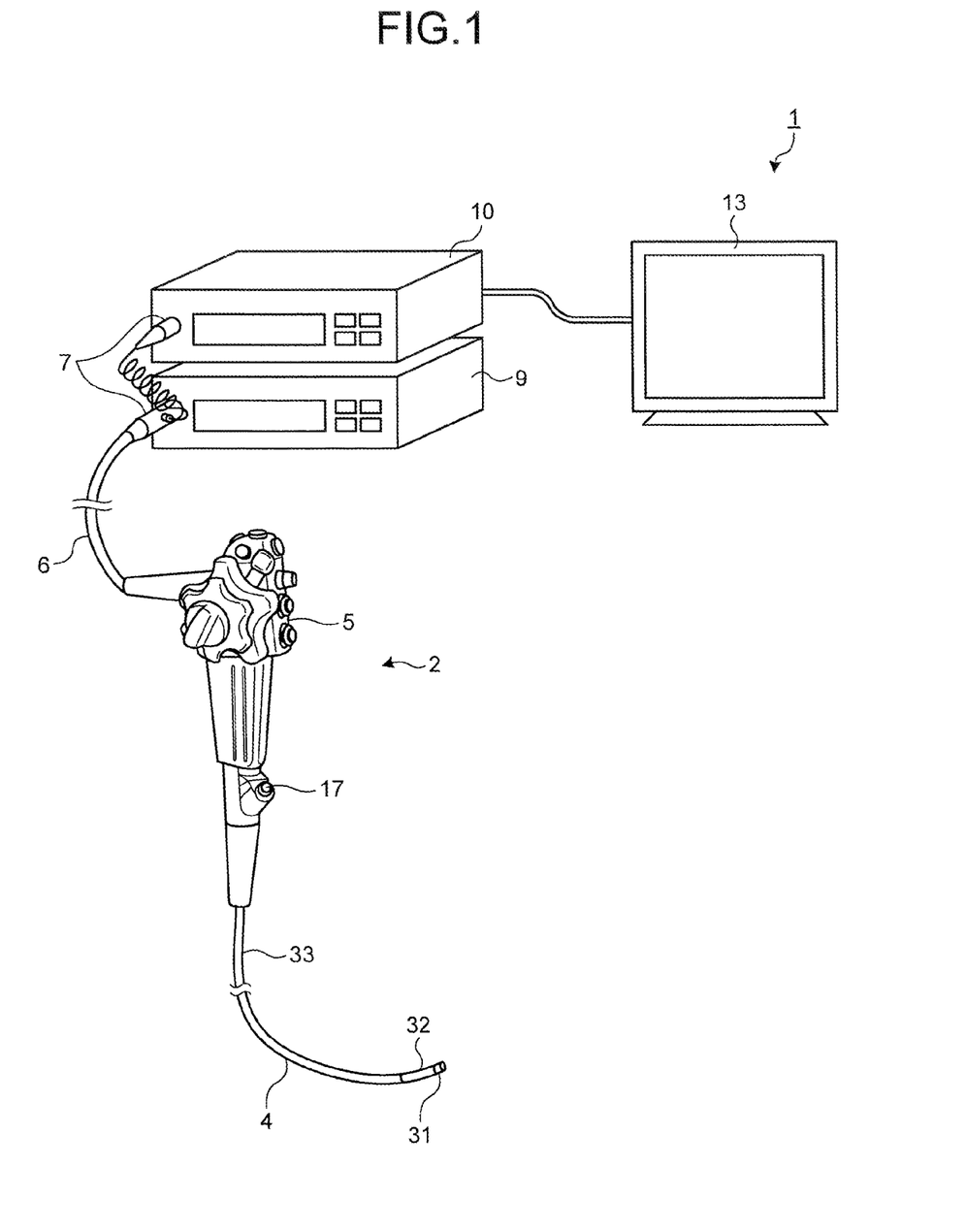
FIG. 1 is a schematic view illustrating an overall configuration of an endoscope system according to an embodiment of the present invention.

FIG. 1 is a schematic view illustrating an overall configuration of an endoscope system according to an embodiment of the present invention. As illustrated in FIG. 1, an endoscope apparatus 1 includes an endoscope 2, a universal code 6, a connector 7, a light source device 9, a processor (control device) 10, and a display device 13.

By inserting an insertion unit 4 inside a body cavity of a subject, the endoscope 2 captures an in-vivo image of the subject and outputs an imaging signal. An electric cable bundle inside the universal code 6 is extended to a distal end of the insertion unit 4 of the endoscope 2 and is connected to an imaging device, which is provided to a distal end portion 31 of the insertion unit 4.

The connector 7 is provided to a proximal end of the universal code 6 and is connected to the light source device 9 and the processor 10. It performs predetermined signal processing on the imaging signal, which has been output by the imaging device of the distal end portion 31 connected to the universal code 6, and it performs analog-digital conversion (A/D conversion) on the imaging signal and outputs it as an image signal.

The light source device 9 is constituted of a white LED, for example. Pulsed white light lit by the light source device 9 passes through the connector 7 and the universal code 6, and it becomes illumination light to be emitted toward an object from the distal end of the insertion unit 4 of the endoscope 2.

The processor 10 performs predetermined image processing on the image signal that has been output from the connector 7 and controls the entire endoscope apparatus 1. The display device 13 displays the image signal that has been processed by the processor 10.

An operating unit 5 provided with a variety of buttons and knobs for operating an endoscope function is connected to a proximal end side of the insertion unit 4 of the endoscope 2. The operating unit 5 is provided with a treatment tool insertion opening 17 through which a treatment tool, such as a biological forceps, an electric knife, and an inspection probe, is inserted into the body cavity of the subject.

The insertion unit 4 is constituted of the distal end portion 31 provided with the imaging device, a bending portion 32 freely bendable in multiple directions and connected to a proximal end side of the distal end portion 31, and a flexible tube portion 33 connected to a proximal end side of the bending portion 32. The bending portion 32 is bent by operating a knob for bending operation provided to the operating unit 5. It is freely bendable in four directions of up, down, right, and left, for example, by pulling and relaxing a bending wire, which is inserted inside the insertion unit 4.

A light guide bundle (not illustrated) that transmits the illumination light from the light source device 9 is arranged to the endoscope 2. An illumination lens (not illustrated) is disposed at an emitting end of the illumination light from the light guide bundle. This illumination lens is provided to the distal end portion 31 of the insertion unit 4, and the illumination light is emitted toward the subject.

Figure 2:
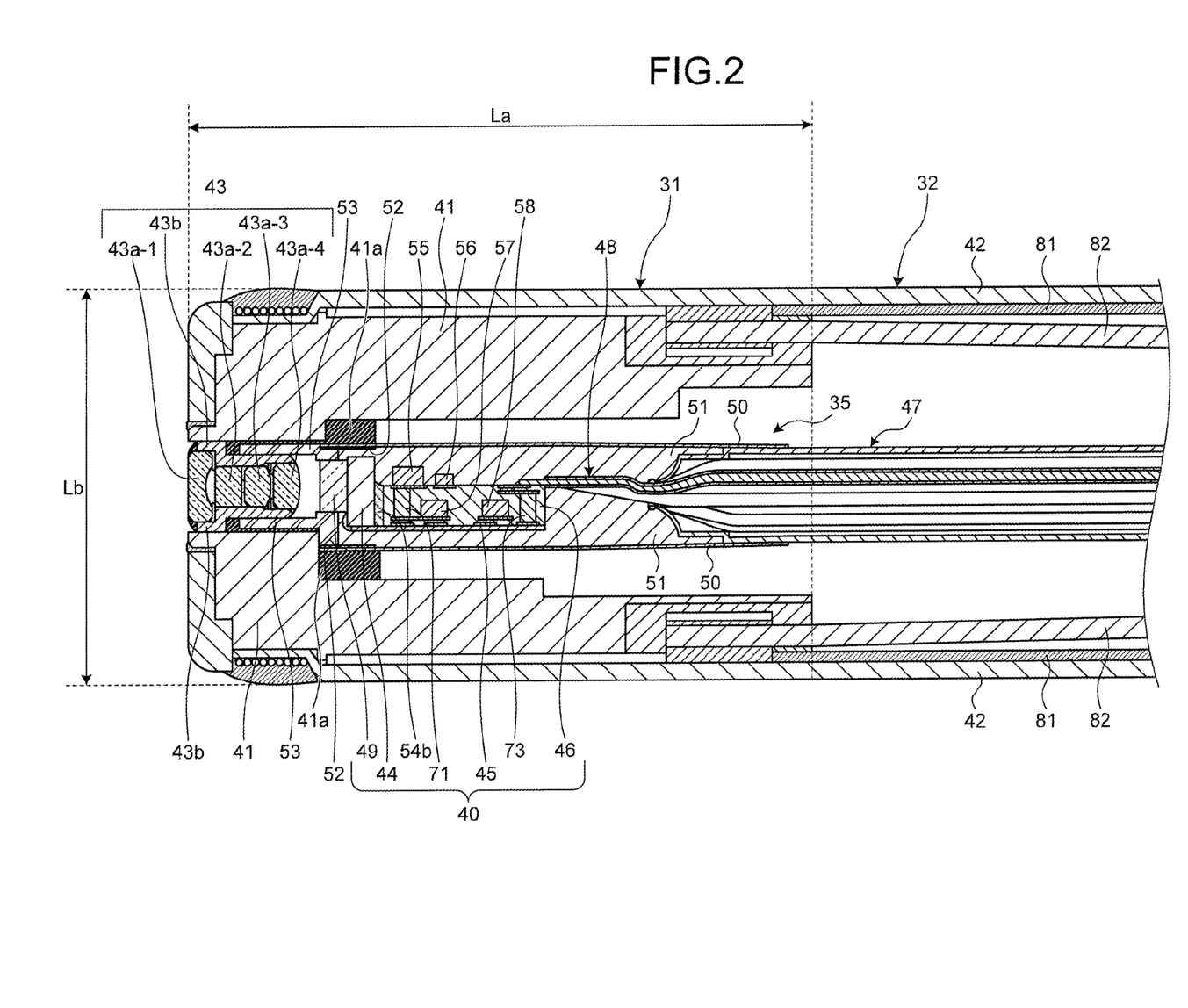
FIG. 2 is a sectional view of a part of a distal end of an endoscope illustrated in FIG. 1.

Next, reference will be made in detail to a configuration of the distal end portion 31 of the endoscope 2. FIG. 2 is a sectional view of a part of a distal end of the endoscope 2. FIG. 2 is a sectional view cut through a surface orthogonal to a substrate surface of the imaging unit, or a surface parallel to an optical axis direction of the imaging unit. The imaging unit is provided to the distal end portion 31 of the endoscope 2. In FIG. 2, the distal end portion 31 and a part of the bending portion 32 of the insertion unit 4 of the endoscope 2 are illustrated.

As illustrated in FIG. 2, the bending portion 32 is freely bendable in four directions of up, down, right, and left by pulling and relaxing a bending wire 82 inserted inside a bending tube 81 disposed inside a covering tube 42 to be described below. An imaging device 35 is provided inside the distal end portion 31, which extends on a distal end side of the bending portion 32.

The imaging device 35 has a lens unit 43 and an imaging unit 40 disposed on a proximal end side of the lens unit 43, which are adhered to inside of a distal end portion main body 41 with an adhesive 41a. The distal end portion main body 41 is constituted of a hard member to form an internal space in which the imaging device 35 is housed. An outer periphery portion of a proximal end of the distal end portion main body 41 is covered with the pliable covering tube 42. Such that the bending portion 32 can be bent, any member that is located on a proximal end side of the distal end portion main body 41 is constituted of a pliable member. The distal end portion 31 in which the distal end portion main body 41 is disposed is a hard part of the insertion unit 4. A length La of this hard part ranges from the distal end of the insertion unit 4 to the proximal end of the distal end portion main body 41. Note that a length Lb corresponds to an outside diameter of the distal end of the insertion unit 4.

The lens unit 43 has a plurality of objective lenses 43a-1 to 43a-4 and a lens holder 43b that holds the objective lenses 43a-1 to 43a-4. A distal end of the lens holder 43b is inserted inside and fixed to the distal end portion main body 41, whereby the lens unit 43 is fixed to the distal end portion main body 41.

The imaging unit 40 includes a solid state image sensor 44 that generates an electric signal by receiving light of a CCD or a CMOS and performing photoelectric conversion thereon, a substrate 45 extending from the solid state image sensor 44 in an optical axis direction, a multi-layer substrate 46 having multiple conductor layers on a surface of the substrate 45, and a glass lid 49 adhered to the solid state image sensor 44 in a state of covering a light-receiving surface of the solid state image sensor 44. To the multi-layer substrate 46 of the imaging unit 40, electronic components 55 to 58 constituting a driving circuit of the solid state image sensor 44 are mounted, and via holes 71 and 73 that electrically conduct between the plurality of conductor layers are formed therein. To a proximal end of the multi-layer substrate 46, a distal end of each of signal cables 48 of an electric cable bundle 47 is connected. Note that on the multi-layer substrate 46, an electronic component other than the ones constituting the driving circuit of the solid state image sensor 44 may also be mounted.

A proximal end of each of the signal cables 48 extends in a direction of a proximal end of the insertion unit 4. The electric cable bundle 47 is inserted and disposed in the insertion unit 4, and it extends to the connector 7 through the operating unit 5 and the universal code 6 illustrated in FIG. 1.

A subject image that has been image-formed by the objective lenses 43a-1 to 43a-4 of the lens unit 43 is detected by the solid state image sensor 44, which is arranged in an image-forming position of the objective lenses 43a-1 to 43a-4, and is converted into an imaging signal. The imaging signal is output to the processor 10 through the signal cables 48, which are connected to the substrate 45 and the multi-layer substrate 46, and the connector 7.

The solid state image sensor 44 is adhered to the substrate 45 and the multi-layer substrate 46. The solid state image sensor 44 and a connecting part of the solid state image sensor 44 and the substrate 45 are covered with a metal reinforcement member 52. To prevent an influence of external static electricity on the electronic components 55 to 58 on the substrate 45, the reinforcement member 52 is installed in a separated manner from the solid state image sensor 44, the substrate 45, and the multi-layer substrate 46.

To improve tolerance, a distal end portion of the imaging unit 40 and the electric cable bundle 47 is covered with a heat shrinkable tube 50 on an outer periphery thereof. Inside the heat shrinkable tube 50, space between components is filled with an adhesive resin 51.

A solid state image sensor holder 53 holds the solid state image sensor 44, which is adhered to the glass lid 49, by fitting an outer periphery surface of the glass lid 49 into an inner periphery surface on the proximal end side of the solid state image sensor holder 53. The outer periphery surface on the proximal end side of the solid state image sensor holder 53 is fitted into an inner periphery surface on a distal end side of the reinforcement member 52. An outer periphery surface on the proximal end side of the lens holder 43b is fitted into the inner periphery surface on the distal end side of the solid state image sensor holder 53. In a state where these members are fitted into each other in this way, the outer periphery surface of the lens holder 43b, the outer periphery surface of the solid state image sensor holder 53, and an outer periphery surface on a distal end side of the heat shrinkable tube 50 are fixed to an inner periphery surface on a distal end of the distal end portion main body 41 with the adhesive 41a.

Figure 3:
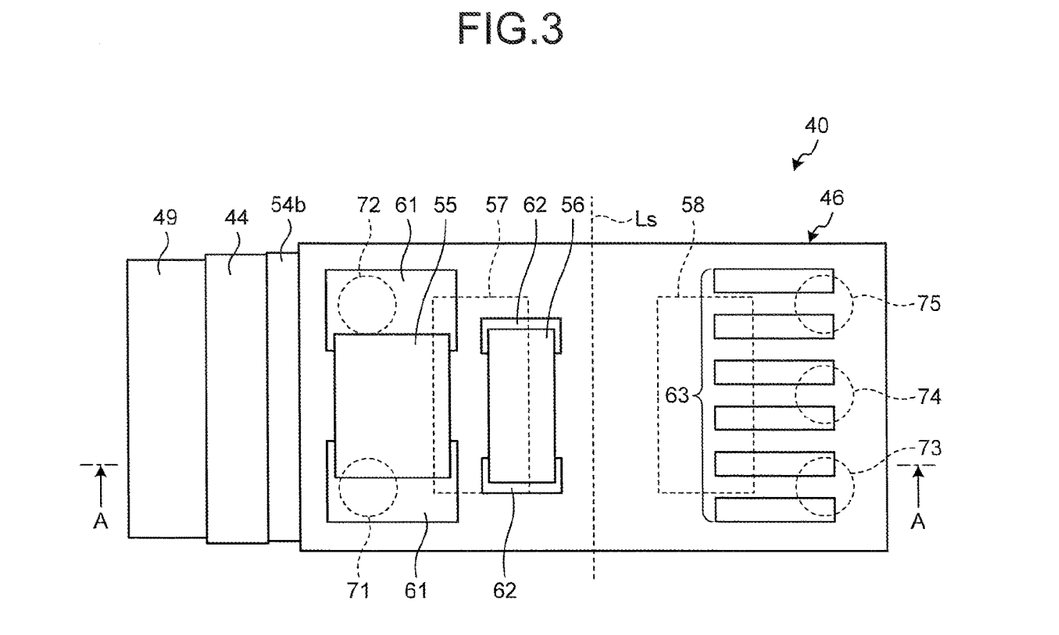
FIG. 3 is a plan view of an imaging unit illustrated in FIG. 2 planarly viewed in a stacking direction.
Figure 4:
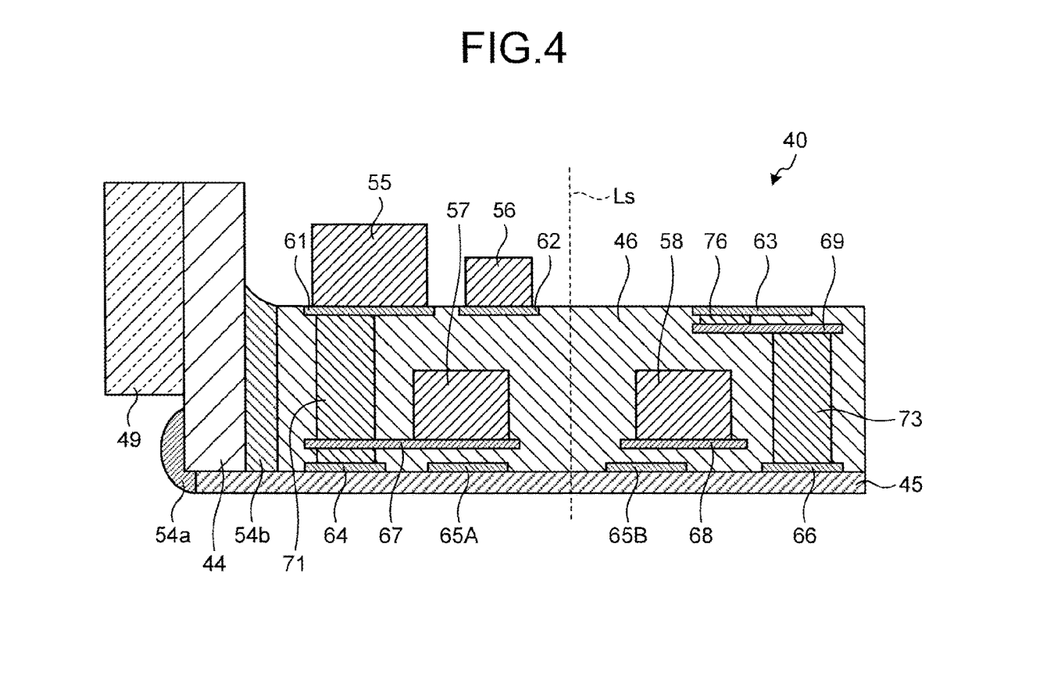
FIG. 4 is a sectional view of line A-A in FIG. 3.

Next, reference will be made to the imaging unit 40. FIG. 3 is a plan view of the imaging unit 40 planarly viewed in a stacking direction. FIG. 4 is a sectional view of line A-A in FIG. 3, or a sectional view when the imaging unit 40 is cut through a surface vertical to a surface of the substrate 45 and parallel to an optical axis direction of the solid state image sensor 44. In FIGS. 3 and 4, for a description purpose, there is illustrated a plane Ls that passes through a center of the multi-layer substrate 46 and bisects a length in an optical axis direction of the multi-layer substrate 46.

As illustrated in FIGS. 3 and 4, in the imaging unit 40, an inner lead (not illustrated) of the substrate 45 is electrically connected to a lower electrode (not illustrated) of the solid state image sensor 44, which are covered with a sealing resin 54a, whereby the solid state image sensor 44 and the substrate 45 are connected to each other.

The substrate 45 is a flexible printed substrate, and it extends from the solid state image sensor 44 in the optical axis direction of the solid state image sensor 44. On the surface of the substrate 45, the multi-layer substrate 46 is formed in which multiple layers are stacked, and the multi-layer substrate 46 is electrically and mechanically connected to the substrate 45. A back surface of the solid state image sensor 44 is adhered to a side surface of the multi-layer substrate 46 on a side of the solid state image sensor 44 with an adhesive 54b.

Among a plurality of electronic components constituting the driving circuit of the solid state image sensor 44, one or more of the electronic components are mounted on an upper surface of the multi-layer substrate 46, and one or more of the electronic components are also embedded inside the multi-layer substrate 46. In the example in FIGS. 3 and 4, among the plurality of electronic components 55 to 58, two electronic components 55 and 56 are mounted on the upper surface of the multi-layer substrate 46. Then, among the plurality of electronic components 55 to 58, two electronic components 57 and 58 are embedded inside the multi-layer substrate 46. The imaging unit 40 is disposed such that the whole imaging unit 40 including the substrate 45, the multi-layer substrate 46, the electronic components 55 to 58, and the signal cables 48 fits within a projection region, which is obtained by projecting the solid state image sensor 44 in the optical axis direction.

On the multi-layer substrate 46, there are formed two connection lands 61 to which the electronic component 55 is electrically connected, two connection lands 62 to which the electronic component 56 is connected, and a cable connection land 63 to which a conductor at a distal end of the signal cable 48 is electrically and mechanically connected. In the example in FIG. 3, six cable connection lands 63 are provided, whereby six signal cables 48 can be connected thereto by solder and the like. On a lower surface of the multi-layer substrate 46, there is formed a plurality of connection lands 64, 65A, 65B, and 66 electrically connected to the substrate 45.

Inside the multi-layer substrate 46, a plurality of conductor layers is layered. In a section illustrated in FIG. 4, conductor layers 67, 68, and 69 are illustrated. Inside the multi-layer substrate 46, a plurality of via holes 71 to 76 is formed. The plurality of conductor layers including the conductor layers 67 to 69 is formed so as to be electrically connected to any of the plurality of via holes 71 to 76.

For example, the connection land 61 on the upper surface of the multi-layer substrate 46, to which the electronic component 55 is electrically connected, is electrically connected to the two connection lands 64 (only one is illustrated in FIG. 4) on a lower surface side of the multi-layer substrate 46 through the via holes 71 and 72 and the conductor layer 67. The connection land 62 on the upper surface of the multi-layer substrate 46, to which the electronic component 56 is electrically connected, is electrically connected to the two connection lands 65A (only one is illustrated in FIG. 4) on the lower surface side of the multi-layer substrate 46 through a via hole that is not illustrated. The electronic component 57, which is embedded in the multi-layer substrate 46, is electrically connected to the conductor layer 67, whereby it is electrically connected to the electronic component 55 and the connection land 64 through the via hole 71. The electronic component 58 is electrically connected to the conductor layer 68, whereby it is electrically connected to the two connection lands 65B (only one is illustrated in FIG. 4) on the lower surface side of the multi-layer substrate 46 through a via hole that is not illustrated. Furthermore, among the cable connection lands 63 on the upper surface of the multi-layer substrate 46, a cable connection land that is the second from the bottom relative to a shorter side direction of the substrate 45 is electrically connected to the connection land 66 on the lower surface side of the multi-layer substrate 46 through the via hole 76, the conductor layer 69, and the via hole 73.

Then, as illustrated in FIGS. 3 and 4, the electronic components 57 and 58 are embedded inside the multi-layer substrate 46 so as to avoid the plane Ls, which passes through a center in the optical axis direction of the multi-layer substrate 46. Then, all of the via holes 71 to 76 are formed on an outer side of the multi-layer substrate 46 in the optical axis direction of the multi-layer substrate 46 relative to the electronic components 57 and 58, which are embedded inside the multi-layer substrate 46. The electronic component 57 and the electronic component 58, which are embedded inside the multi-layer substrate 46, are embedded inside the multi-layer substrate 46 so as to be adjacent to each other without interposing any via hole. In this embodiment, in a case where two or more electronic components are embedded inside the multi-layer substrate 46, these two or more electronic components are embedded inside the multi-layer substrate so as to be adjacent to each other without interposing any via hole. The electronic components 57 and 58 are embedded in a part near the center in the optical axis direction of the multi-layer substrate 46, and the via holes 71 to 76 are formed in a part at an end in the optical axis direction of the multi-layer substrate 46 outside the electronic components 57 and 58. Note that in the imaging unit 40 illustrated in FIGS. 3 and 4, a long side direction of the substrate 45 and the multi-layer substrate 46 corresponds to the optical axis direction whereas a shorter side direction of the substrate 45 and the multi-layer substrate 46 corresponds to a direction orthogonal to both of the optical axis direction and the stacking direction.

Figure 5:
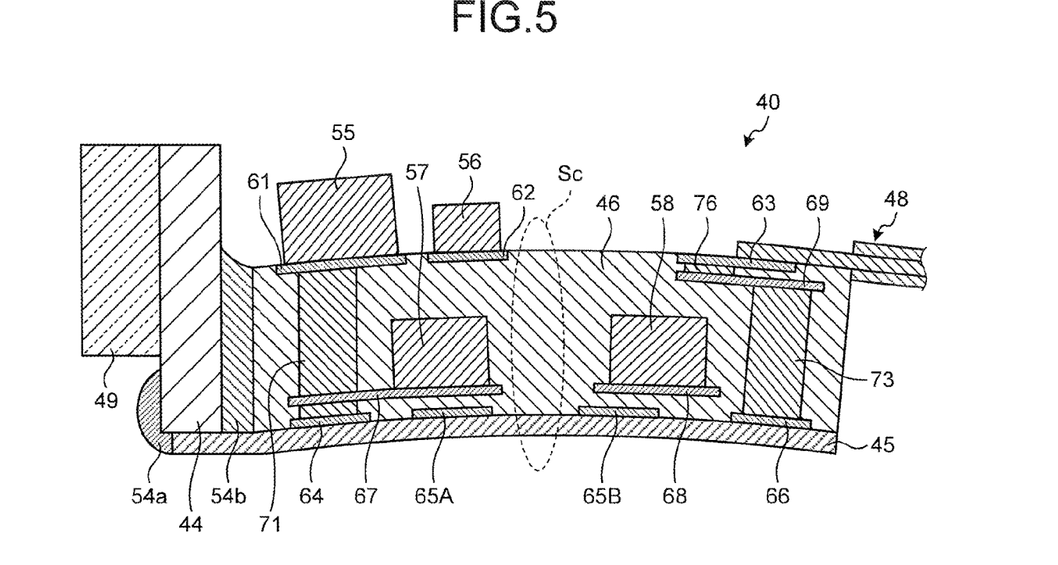
FIG. 5 is a schematic view illustrating a force applied to the imaging unit illustrated in FIG. 3 and is a sectional view of the imaging unit.

Here, in the endoscope apparatus 1, accompanied with forward and backward operation of an insertion unit as well as a bending movement thereof for adjusting a camera angle during use of an endoscope, a force pushing in a distal end direction or a force shaking up and down and twisting is applied to the signal cable 48. In a case where a stress is caused to the multi-layer substrate 46 and the substrate 45, to which the signal cables 48 are connected, due to this, as illustrated in FIG. 5, a central part Sc of the substrate 45 and the multi-layer substrate 46 may be bent.

In general, an electronic component is formed of a hard material such as ceramic, whereby the electronic component itself is relatively less deformable by the bending stress unique to the endoscope. In contrast, a via hole is more susceptible to the bending stress than the electronic component. When an excessive stress is applied to the via hole, accompanied by deformation of a multi-layer substrate, a land or a conductor layer to which the via hole is connected may also be deformed, whereby it may be peeled off from the via hole. When such peeling off of the land or the conductor layer from the via hole occurs, conduction of the via hole becomes unstable, whereby it may cause degradation of performance of the imaging unit such as occurrence of noise in an image.

In the imaging unit 40, component arrangement is set such that the electronic components 57 and 58 are embedded in a part near the center in the optical axis direction of the multi-layer substrate 46, and the via holes 71 to 76 are formed in the part at an end in the optical axis direction of the multi-layer substrate 46 outside the electronic components 57 and 58. Then, in the imaging unit 40, at the center of the multi-layer substrate 46, none of the via holes 71 to 76 and the electronic components 57 and 58 is disposed. Thus, as in FIG. 5, since the electronic components 57 and 58 and the via holes 71, 73, and 76 are not located at the central part Sc of the multi-layer substrate 46 where a bend is caused by the stress, these are not affected by the stress. In addition, in the imaging unit 40, the via holes 71 to 76 are disposed near the end in the optical axis direction of the multi-layer substrate 46 where the stress is less likely to be applied and is less deformable than the central part, whereby an influence of the stress on the via holes 71 to 76 is suppressed as much as possible. Thus, in the imaging unit 40, it is possible to reduce instability of the conduction of the via holes 71 to 76 and to achieve high reliability.

In addition, since the back surface of the solid state image sensor 44 is adhered and fixed to the side surface of the multi-layer substrate 46 on a side of the solid state image sensor 44 where the electronic component is mounted with the adhesive 54b, strength of this part is enhanced. Thus, even if a twisting force is applied due to the bending movement thereof for adjusting a camera angle and the like, deformation such as a warp and a bend is less likely to be caused to the substrate 45 and the multi-layer substrate 46.

Then, in the imaging unit 40, the electronic components 57 and 58 are embedded inside the multi-layer substrate 46 on an inner side relative to the via holes 71 to 76. Thus, in the imaging unit 40, it is possible to install the electronic components 57 and 58 in a position where the two electronic components 55 and 56 mounted on the upper surface of the multi-layer substrate 46 are superimposed on the connection lands 61 and 62 of the electronic components 55 and 56 in a top view. Accordingly, in the imaging unit 40, it is possible to reduce an area of the substrate in the top view compared to a configuration having a component arrangement of disposing all of four electronic components in addition to the cable connection land on the upper surface of the multi-layer substrate, whereby it is possible to achieve a compact imaging unit.

Figure 6:
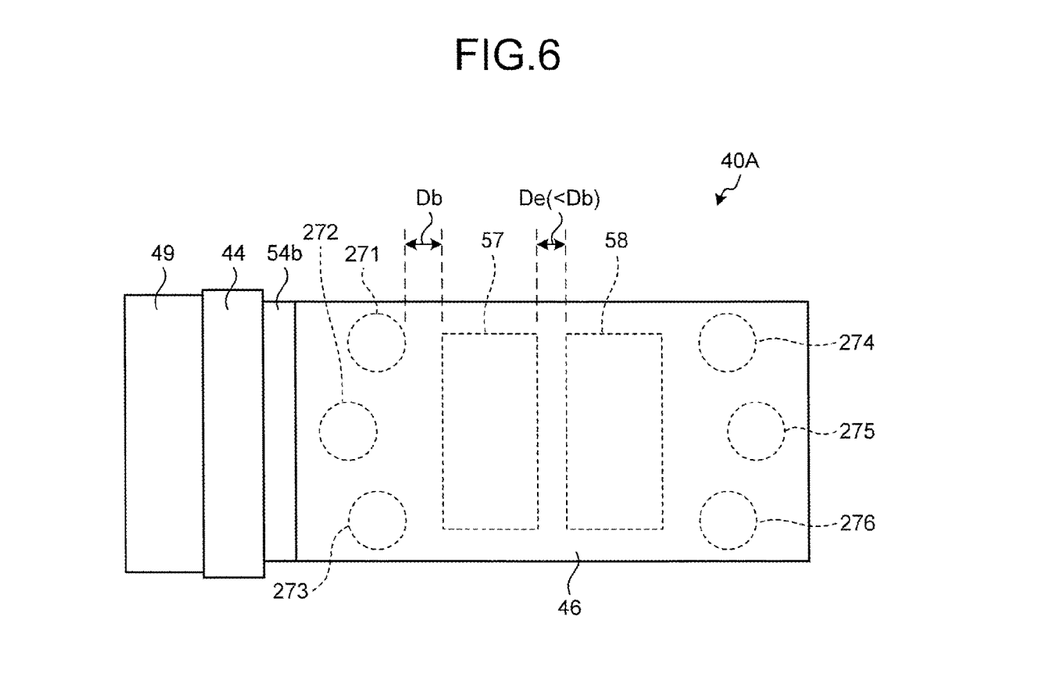
FIG. 6 is a plan view of another example of the imaging unit illustrated in FIG. 2 planarly viewed in the stacking direction.

In this embodiment, as illustrated in the plan view in FIG. 3, three via holes 73 to 75 are disposed at an end of the substrate 45 on the same straight line parallel to the shorter side direction of the multi-layer substrate 46; however, the component arrangement is not limited to this. For example, in a case where three or more via holes are disposed at the end of the substrate, as an imaging unit 40A illustrated in FIG. 6, three via holes 271 to 273 on a solid state image sensor 44 side may be disposed zigzag along a direction orthogonal to an optical axis. In the same way, three via holes 274 to 276 on a proximal end side may also be disposed zigzag along the direction orthogonal to the optical axis. In a case where the via holes are disposed in this way, with a minimum amount of extension of the substrate in the optical axis direction, a width in the shorter side direction of the substrate and the multi-layer substrate can be reduced while securing an interval between the via holes. In the example in FIG. 6, in order to reduce the amount of extension of the multi-layer substrate 46 in the optical axis direction, a zigzag arrangement close to a straight line is used by reducing the interval between the adjacent via holes. In FIG. 6, illustration of the electronic components and the connection lands mounted on the upper surface of the multi-layer substrate 46 is omitted for a description purpose.

In a case where two or more electronic components are embedded in the multi-layer substrate, as illustrated in FIG. 6, the electronic components 57 and 58 are embedded in the central part of the multi-layer substrate 46 along the optical axis direction without interposing the via holes 271 to 276 therebetween. Since it is possible to mount the electronic components at high density by a surface mount technology, among two or more electronic components embedded in the multi-layer substrate 46 of the plurality of electronic components 55 to 58, the interval between two or more adjacent electronic components may be an interval De that is smaller than a minimum value Db of the interval between the via hole formed inside the multi-layer substrate 46 and the electronic components embedded inside the multi-layer substrate 46. In addition, since the electronic component is formed of the hard material as described above, it is relatively less deformable by the bending stress unique to the endoscope. Accordingly, the influence of the stress on the electronic component is small, whereby it is possible to embed the two electronic components 57 and 58 in a proximate state inside the multi-layer substrate 46 at the central part thereof. Thus, the component arrangement in which the two electronic components 57 and 58 are embedded in the proximate state without interposing a via hole inside the multi-layer substrate near the center thereof as well as the via holes 271 to 276 are formed at the end in the optical axis direction of the multi-layer substrate 46 may be the most preferred component arrangement of this embodiment because the length in the optical axis direction of the multi-layer substrate 46 can be reduced the most while securing the interval between each of the members.

Figure 7:
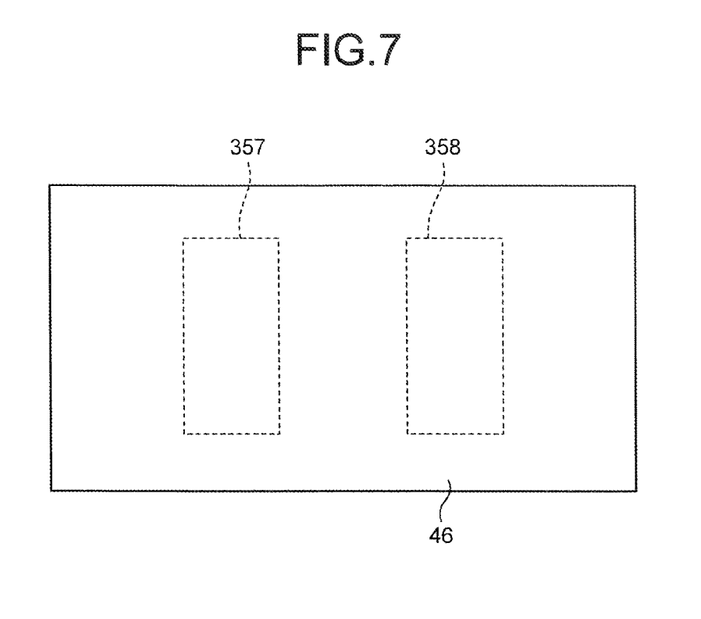
FIG. 7 is a plan view illustrating a method of arranging an electronic component used in the embodiment.
Figure 8:
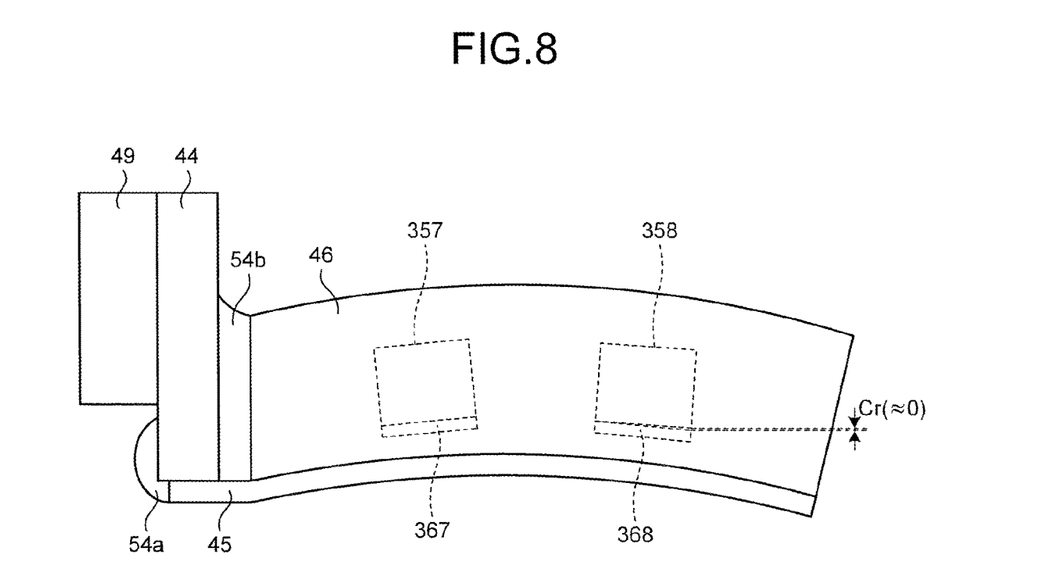
FIG. 8 is a schematic view illustrating how the imaging unit illustrated in FIG. 7 is deformed by receiving a stress.
Figure 9:
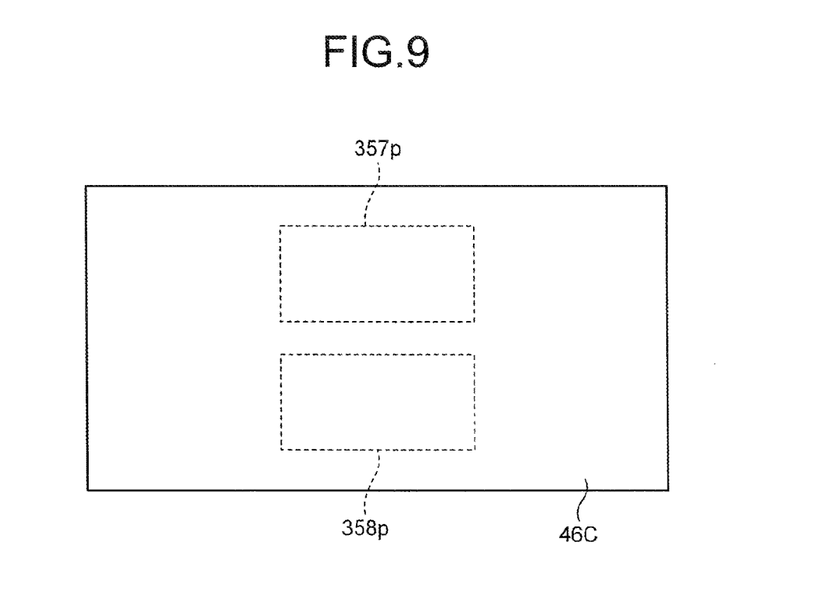
FIG. 9 is a plan view illustrating a method of arranging the electronic component not used in the embodiment.
Figure 10:
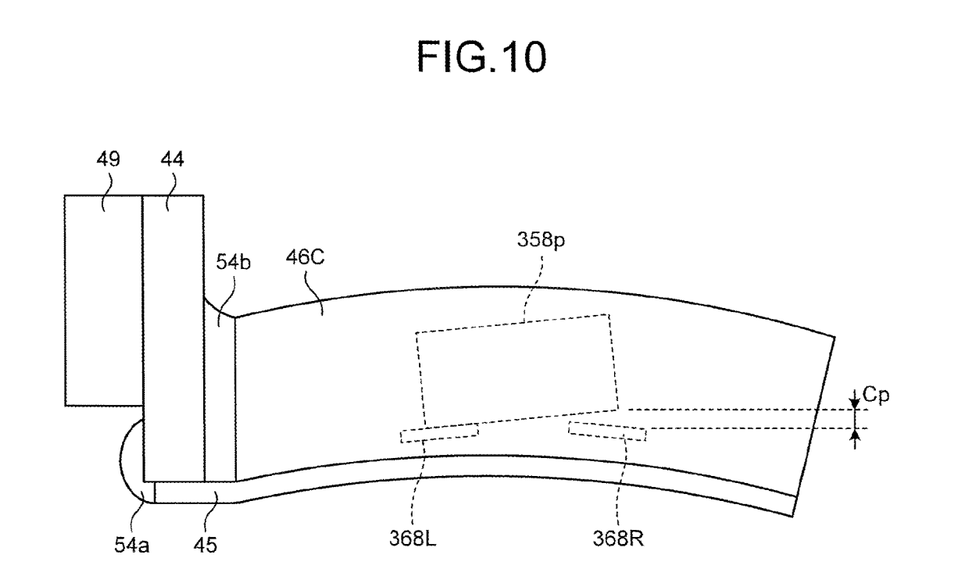
FIG. 10 is a schematic view illustrating how the imaging unit illustrated in FIG. 9 is deformed by receiving a stress.

Reference will be made to a direction of the electronic component embedded inside the multi-layer substrate 46. FIG. 7 is a schematic view illustrating a method of arranging the electronic component used in the embodiment, and it is a plan view of the imaging unit planarly viewed in the stacking direction. In FIG. 7, for a description purpose, illustration of a member other than the multi-layer substrate and the electronic component is omitted. FIG. 8 is a schematic view illustrating how the imaging unit illustrated in FIG. 7 is deformed by receiving the stress. In FIG. 8, the deformed imaging unit is viewed in the direction orthogonal to both of the optical axis direction and the stacking direction. FIG. 9 is a plan view illustrating a method of arranging the electronic component not used in the embodiment, and it is a plan view planarly viewed in the stacking direction. FIG. 10 is a schematic view illustrating how the imaging unit illustrated in FIG. 9 is deformed by receiving the stress. In FIG. 10, the deformed imaging unit is viewed in the direction orthogonal to both of the optical axis direction and the stacking direction.

As illustrated in FIG. 7, in the embodiment, in a case where both of electronic components 357 and 358 embedded inside the multi-layer substrate 46 are rectangular when planarly viewed in the stacking direction, the electronic components 357 and 358 are disposed such that a long side of a rectangle is in a direction orthogonal to the optical axis direction of the multi-layer substrate 46. When an upward stress is generated on the substrate, the multi-layer substrate 46 is deformed according to the stress as illustrated in FIG. 8. In contrast, the electronic components 357 and 358 are less deformable; however, since a length in the optical axis direction of the electronic components 357 and 358 is small relative to that of the multi-layer substrate 46, even in a case where the electronic components 357 and 358 are not capable of following the deformation of the multi-layer substrate 46, a width Cr (see FIG. 8) of lifting of the electronic components 357 and 358 from conductor layers 367 and 368 is very small, whereby performance of the imaging unit is hardly degraded.

On the other hand, as illustrated in FIG. 9, in a case where electronic components 357$p$ and 358$p$ are disposed such that the long side of the rectangle is parallel to an optical axis direction of a multi-layer substrate 46C, a length in the optical axis direction of the electronic components 357$p$ and 358$p$ is long relative to that of the multi-layer substrate 46C. Since the electronic components 357$p$ and 358$p$ are less deformable, when the multi-layer substrate 46C is deformed, the electronic component 358$p$ is not capable of following the deformation of the multi-layer substrate 46C, whereby it may peel off from conductor layers 368R and 368L (see FIG. 10), which are deformed following the deformation of the multi-layer substrate 46C. Specifically, as illustrated in FIG. 10, the electronic component 358$p$ peels off from an upper surface of the conductor layer 368R, and a lower surface of the electronic component 358$p$ is lifted from the upper surface of the conductor layer 368R by a width Cp, which is large compared to the width Cr. As a result, conduction between the electronic component 358$p$ and the conductor layer 368R becomes unstable, and the performance of the imaging unit may be degraded.

Thus, in this embodiment, in a case where a planar shape of the electronic component embedded inside the multi-layer substrate is a rectangle when planarly viewed in the stacking direction, by disposing the electronic component such that the long side of the rectangle is in an direction orthogonal to the optical axis direction of the multi-layer substrate, it is possible to reduce the influence of the stress on the electronic component is reduced, whereby stabilization of the performance of the imaging unit is achieved.

According to some embodiments, at least one of electronic components is embedded in a multi-layer substrate to achieve a compact distal end of the insertion unit. In addition, a via hole, which is susceptible to the stress unique to the endoscope apparatus, is formed in a position which is outside of the electronic components along an optical axis direction of the multi-layer substrate so as to be less susceptible to a bend and a warp. With this component arrangement, it is possible to reduce an influence of the stress unique to the endoscope apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit provided at a distal end of an endoscope, the imaging unit comprising:
   a solid state image sensor configured to receive light and perform photoelectric conversion on the light to generate an electric signal;
   a substrate extending from the solid state image sensor in an optical axis direction of the solid state image sensor;
   a multi-layer substrate formed on a surface of the substrate, the multi-layer substrate having a plurality of electronic components mounted thereon, the multi-layer substrate having a plurality of conductor layers and a plurality of via holes formed therein, the solid state image sensor being positioned on a distal end of the multi-layer substrate; and
   a signal cable connected to a proximal end of the multi-layer substrate;

wherein the plurality of electronic components are disposed in a position excluding a center of the multi-layer substrate in the optical axis direction, at least one of the plurality of electronic components is embedded inside the multi-layer substrate, and the plurality of via holes are formed on both sides of the at least one of the plurality of electronic components embedded inside the multi-layer substrate along an optical axis direction of the multi-layer substrate.

2. The imaging unit according to claim 1, wherein the multi-layer substrate has two or more electronic components among the plurality of electronic components embedded therein, and the two or more electronic components are adjacently embedded inside the multi-layer substrate such that the plurality of via holes is not interposed between the two or more electronic components.

3. The imaging unit according to claim 1, wherein the at least one of the plurality of electronic components is embedded in a central part of the multi-layer substrate.

4. The imaging unit according to claim 1, wherein the at least one of the plurality of electronic components embedded inside the multi-layer substrate has a rectangular shape in a plan view in a stacking direction, and is disposed such that a long side of the rectangular shape is orthogonal to the optical axis direction of the multi-layer substrate.

5. The imaging unit according to claim 2, wherein among the two or more electronic components embedded inside the multi-layer substrate, an interval between the adjacent electronic components is smaller than a minimum value of an interval between the plurality of via holes formed inside the multi-layer substrate and the two or more electronic components embedded inside the multi-layer substrate.

6. The imaging unit according to claim 1, wherein a back surface of the solid state image sensor is adhered to a side surface of the multi-layer substrate.

7. The imaging unit according to claim 1, wherein the optical axis direction of the multi-layer substrate is a direction in which the multi-layer substrate extends from the solid state image sensor, and the plurality of via holes are formed on an outer side of the at least one of the plurality of electronic components embedded inside the multi-layer substrate along the optical axis direction of the multi-layer substrate.

8. An endoscope apparatus comprising:

an insertion unit having an imaging unit at a distal end of the insertion unit, wherein the imaging unit comprises:

a solid state image sensor configured to receive light and perform photoelectric conversion on the light to generate an electric signal;

a substrate extending from the solid state image sensor in an optical axis direction of the solid state image sensor;

a multi-layer substrate formed on a surface of the substrate, the multi-layer substrate having a plurality of electronic components mounted thereon, the multi-layer substrate having a plurality of conductor layers and a plurality of via holes formed therein, the solid state image sensor being positioned on a distal end of the multi-layer substrate; and a signal cable connected to a proximal end of the multi-layer substrate;

wherein the plurality of electronic components are disposed in a position excluding a center of the multi-layer substrate in the optical axis direction, at least one of the plurality of electronic components is embedded inside the multi-layer substrate, and the plurality of via holes are formed on both sides of the at least one of the plurality of electronic components embedded inside the multi-layer substrate along an optical axis direction of the multi-layer substrate.

* * * * *